United States Patent [19]

Romer et al.

[11] Patent Number: 5,631,207

[45] Date of Patent: May 20, 1997

[54] USE OF 5-ALKYL-1,3,4-OXADIAZOL (AND THIADIAZOL)-2-THIOMETHYLTHIOCYANATES AS MARINE ANTIFOULING AGENTS

[75] Inventors: Duane R. Romer; Ravi B. Shankar; R. Garth Pews, all of Midland, Mich.

[73] Assignee: The Dow Chemical Company, Midland, Mich.

[21] Appl. No.: 678,025

[22] Filed: Jul. 10, 1996

[51] Int. Cl.$^6$ .......................... A01N 43/36; A01N 43/82
[52] U.S. Cl. .......................... 504/156; 210/749; 210/764; 514/363; 514/364

[58] Field of Search .......................... 504/156; 210/749, 210/764; 514/363, 364

[56] References Cited

FOREIGN PATENT DOCUMENTS 2541388  9/1975  Germany.

Primary Examiner—Allen J. Robinson
Attorney, Agent, or Firm—S. Preston Jones; James M. Pelton

[57] ABSTRACT

Disclosed is the use of compositions employing 5-alkyl-1, 3,4-oxadiazol(or thiadiazol)-2-thiomethylthiocyanates as the active marine antifouling agent.

7 Claims, No Drawings

USE OF 5-ALKYL-1,3,4-OXADIAZOL (AND THIADIAZOL)-2-THIOMETHYLTHIOCYANATES AS MARINE ANTIFOULING AGENTS

FIELD OF THE INVENTION

The present invention is directed to the use of 5-alkyl-1,3,4-oxadiazol-2-thiomethylthiocyanates and 5-alkyl-1,3,4-thiadiazol-2-thiomethylthiocyanates as marine antifouling agents.

BACKGROUND OF THE INVENTION

The 5-alkyl-1,3,4-oxadiazol-2-thiomethylthiocyanate and 5-alkyl-1,3,4-thiadiazol-2-thiomethylthiocyanates compounds are known and taught by Staller et al. in German Patent Offenlegungsschrift 25 41 388. These compounds are taught to be useful as plant fungicides.

SUMMARY OF THE INVENTION

The present invention is directed to the use of 5-alkyl-1,3,4-oxadiazol-2-thiomethylthiocyanates and 5-alkyl-1,3,4-thiadiazol-2-thiomethylthiocyanates which corresponds to the formula:

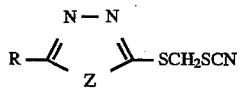

wherein R represents a $C_1$-$C_{12}$ straight or branched chain alkyl radical and Z is oxygen or sulfur as marine antifouling agent.

Compositions or formulations containing 5-alkyl-1,3,4-oxadiazol-2-thiomethylthiocyanates or 5-alkyl-1,3,4-thiadiazol-2-thiomethylthiocyanates as the active marine antifouling agent are employed to treat surfaces exposed to a marine environment in which marine organisms grow so as to prevent the growth of said marine organisms on said surfaces.

DETAILED DESCRIPTION OF THE INVENTION

The 5-alkyl-1,3,4-oxadiazol(and thiadiazol)-2-thiomethylthiocyanates employed in the practice of the present invention are known compounds and can be prepared by the reaction of an appropriate ((5-alkyl-1,3,4-oxadiazole(or thiadiazole-2-yl)thio)halomethyl ester with an alkaline thiocyanate in a solvent as taught by Staller et al. in German Patent Offenlegungsschrift 25 41 388.

The following examples illustrate the present invention and the manner by which it can be practiced but, as such, should not be construed as limitations upon the overall scope of the same.

Since the hereinabove and hereinafter set forth compound preparation procedures employ only standard chemistry practices and it is known that slightly different reactants can require slightly different reaction parameters from those for other reactants, it is to be understood that minor modifications to the reaction parameters set forth such as the use of an excess of one reactant, the use of a catalyst, the use of temperatures slightly higher than room temperature and/or high speed mixing and other such conventional changes are within the scope of the present invention.

The structure identity of the compound was confirmed by proton nuclear magnetic resonance spectroscopy ($^1$H NMR), recorded at 300 MHz; carbon nuclear magnetic resonance spectroscopy ($^{13}$C NMR) recorded at 75 MHz; infrared spectroscopy (IR) and mass spectrometry (MS). The reaction is conducted under a positive pressure of nitrogen.

EXAMPLE I

5-η-Nonanoyl-1,3,4-oxadiazole-2-thiomethylthiocyanate

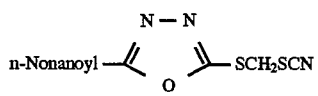

To a solution of (0.05 mol) of ((5-η-nonanoyl-1,3,4-oxadiazol-2-yl)thio)chloromethyl ester in 100 mL of dimethylformamide was added (0.1 mol) of potassium thiocyanate. The solution was heated at 60°–65° C. for 24 hours, cooled to room temperature and poured into 250 mL of water. The resulting mixture was extracted three times with 100 mL portions of ether; the extracts were combined, washed with water followed by washing with brine and then dried. Concentration of the mixture followed by flash chromatography, eluting with 20 percent ethyl acetate/hexanes gave the title compound as an orange solid in a yield of 41 percent of theoretical. $^1$H NMR (CDCl$_3$) δ 4.80 (s, 2H), 2.87 (t, J=7.4 Hz, 2H), 179 (m, 2H), 1.27 (m, 12H), 0.88 (t, J=5.6 Hz, 3H); $^{13}$C NMR (CDCl$_3$) δ 169.18, 162.69, 110.65, 37.31, 31.78, 29.29, 29.28, 29.03, 28.89, 26.26, 25.39, 22.62, 14.08.

EXAMPLE II

5-η-propyl-1,3,4-oxadiazole-2-thiomethylthiocyanate

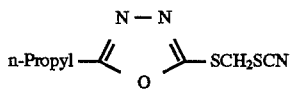

Following the preparative procedure of Example I, employing the appropriate ((5-n-propyl-1,3,4-oxadiazol-2-yl)thio)chloromethyl ester reactant, the title compound was prepared as an orange solid in a yield of 41 percent of theoretical. $^1$H NMR (CDCl$_3$) δ 4.76 (s, 2H), 2.85 (t, J=7.4 Hz, 2H), 1.84 (m, 4H), 1.04 (t, J=7.3 Hz, 3H); $^{13}$C NMR (CDCl$_3$) δ 169.51, 161.16, 111.14, 37.60, 27.62, 20.20, 13.91.

EXAMPLE III

5-η-pentyl-1,3,4-oxadiazole-2-thiomethylthiocyanate

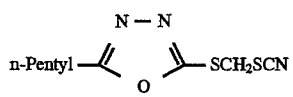

Following the preparative procedure of Example I, employing the appropriate ((5-η-pentyl-1,3,4-oxadiazol-2-yl)thio)chloromethyl ester reactant, the title compound was prepared as an orange solid in a yield of 38 percent of theoretical. $^1$H NMR (CDCl$_3$) δ 5.20 (s, 2H), 2.88 (t, J=8.0 Hz, 2H), 1.78 (m, 2H), 1.35 (m, 4H), 0.90 (t, J=7.3 Hz, 3H); $^{13}$C NMR (CDCl$_3$) δ 169.00, 160.68, 45.14. 30.90, 25.90, 25.26, 22.26, 13.70.

EXAMPLE IV 5-methyl-1,3,4-oxadiazole-2-thiomethylthiocyanate

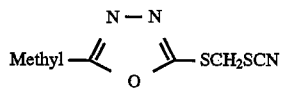

Following the preparative procedure of Example I, employing the appropriate ((5-methyl-1,3,4-oxadiazol-2-yl) thio)chloromethyl ester reactant, the title compound was prepared as a clear oil in a yield of 87 percent of theoretical. $^1$H NMR (CDCl$_3$) δ 4.80 (s, 2H), 2.58 (s, 3H); $^{13}$C NMR (CDCl$_3$) δ 160.65, 110.52, 36.50, 10.84.

EXAMPLE V 5-methyl-1,3,4-thiadiazole-2-thiomethylthiocyanate

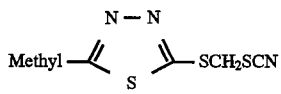

Following the preparative procedure of Example I, employing the appropriate ((5-methyl-1,3,4-thiadiazol-2-yl) thio)chloromethyl ester reactant, the title compound was prepared as a light yellow oil in a yield of 39 percent of theoretical. $^1$H NMR (CDCl$_3$) δ 4.89 (s, 2H), 2.78 (s, 3H); $^{13}$C NMR (CDCl$_3$) δ 165.99, 160.50, 110.92, 37.70, 15.46.

Preparation of Starting Materials:

The ((5-alkyl-1,3,4-oxadiazole(and thiadiazole)-2-yl) thio)chloromethyl esters employed as starting materials are well known compounds and can be prepared as taught in German Patent Offenlegungsschrift 25 41 388.

Marine Antifouling Activity

The present invention is directed to a method for inhibiting marine organisms. The term "marine organisms" is meant to include marine animals, such as barnacles, serpulid, bryozoa, oysters and hydroids, and marine plants, such as green algae and brown algae. The method for inhibiting marine organisms comprises contacting a surface exposed to a marine environment in which marine organisms grow with a composition containing a marine antifouling effective amount of one of the active compounds of this invention.

As appreciated by those skilled in the art, there may be some variation in marine antifouling potency and spectrum of marine antifouling activity dependent on various factors including the specific materials with which the active compound is formulated.

As used herein, the term "marine antifouling effective amount" refers to that amount of the active compound of this invention needed to exhibit inhibition of selected marine organisms. Typically, this amount varies from providing about 1 weight percent to about 30 weight percent of the compound to a marine antifouling composition which is used to treat a surface exposed to a marine environment in which marine organisms live or grow. Such amounts vary depending upon the particular marine organism to be treated. Also, the exact concentration of the compound to be added in the preparation of industrial and consumer formulations may vary within a product type depending upon the specific compound and the specific components of the formulation.

A composition comprising a marine antifouling effective amount of the active compound will also comprise an inert diluent which may be, for example, in the form of a paint. Particularly preferred are those paints having a vinyl resin binder such as, for example, a plasticized polyvinyl chloride or a polyvinyl chloride-polyvinyl acetate type. Preferably, the binders are formulated as latexes or emulsions. In a paint composition, the compound of the present invention is preferably used in an amount from about 1 to about 30 weight percent and, most preferably, from about 10 to about 25 weight percent. In addition to vinyl resin binder paints, epoxy and polyurethane binder paints containing the compound may also be useful. Coatings and films prepared from paints comprising the compound of the present invention typically remain substantially free from build-up of marine organisms for periods ranging from about 3 to about 12 months, depending upon the concentration of the compound and the thickness of the applied coating or film.

The term "a surface exposed to a marine environment" refers to a surface where a marine organism naturally or normally lives or grows. Typically, such a surface will be an area that is in continual or periodic contact with a marine environment such as an ocean or other body of water. Typical surfaces include, for example, a ship hull.

The marine antifouling activity of the compounds of the present invention is demonstrated by the following techniques.

Test panels are prepared from clear, rigid polyvinyl chloride film that is $0.381 \times 10^{-3}$ m thick and has one textured surface. The test panels are 0.1524 m by 0.1524 m squares that have 0.00635 m holes punched at corners on 0.127 m centers. A 0.102 square template, with a 0.067 m diameter hole at the center, is attached to the center of the textured surface of the test panels.

The candidate marine antifoulant compound (1.0 g) is stirred into a resinous latex binder (9.0 g). A portion of the compound/binder mixture (1.5 g) is added to the center of the test panel and uniformly spread over the circular area inside the template.

Water is added dropwise as needed to properly spread the compound/binder mixture. The template prevents the compound/binder mixture from spreading beyond the uncovered area. The test panel is allowed to sit for between 10 to 30 minutes until the edge of the spread compound/binder mixture has dried. The template is then removed. The test panel is then allowed to dry for 8 to 12 hours at room temperature.

Two test panels are prepared for each candidate marine antifoulant compound. Two control test panels are also prepared by only treating with the resinous latex binder. One test panel of each candidate marine antifoulant compound is attached over a white background to the topside of an exposure support apparatus. The second test panel is attached over a black background to the underside of the exposure support apparatus. The exposure support apparatus is placed horizontally 0.0254 m under a marine surface with the white background topside facing up. The exposure support apparatus is exposed to the marine environment for both 6 and 10 weeks during which time the control test panels become substantially covered with mature marine organism growth on both the topside and underside exposures.

After being removed from the exposure support apparatus, each test panel is inspected and rated for marine organism growth on both the treated and untreated areas of the test panel. The marine organisms present on the treated and untreated areas are noted. The presence of algae spores and bacterial slime are noted but not included in rating each test panel. The test panels are rated on a scale from 10 (representing completely free of marine organism growth) to 0 (representing completely covered with marine organism growth).

In Table I, the marine antifouling rating values for various 5-alkyl-1,3,4-oxadiazole-2-thiomethylthiocyanates is set forth, as well as the ratings for control panels (with no marine antifouling compound and referred to as "Control").

TABLE I

Marine Antifouling Rating for Test Compounds

| | Marine Antifouling Ratings | | | | | |
|---|---|---|---|---|---|---|
| | Top Panel at indicated time in weeks | | | Bottom Panel at indicated time in weeks | | |
| Test Compound | 6 | 10 | 16 | 6 | 10 | 16 |
| 5-methyl-1,3,4--oxadiazole-2--thiomethylthiocyanate | 2 | 2 | — | 7 | 5 | — |
| 5-methyl-1,3,4--thiadiazole-2--thiomethylthiocyanate | 9 | 2 | — | 3 | 2 | — |
| 5-η-Nonanoyl-1,3,4--oxadiazole-2--thiomethylthiocyanate | 10 | 9 | 9 | 10 | 8 | 1 |
| Control | 6 | 3 | — | 0 | 0 | — |

What is claimed is:

1. A method for preventing the growth of marine organisms on a surface exposed to a marine environment in which marine organisms grow which comprises contacting said surface with a composition containing an inert diluent and a marine antifouling effective amount of an active 5-alkyl-1,3,4-oxadiazole-(or thiadiazole)-2-thiomethylthiocyanate compound which corresponds to the formula:

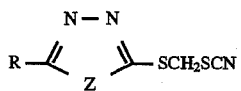

wherein R represents a $C_1$–$C_{12}$ straight or branched chain alkyl radical and Z is oxygen or sulfur.

2. The method as claimed in claim 1 wherein the active compound is 5-methyl-1,3,4-oxadiazole-2-thiomethylthiocyanate.

3. The method as claimed in claim 1 wherein the active compound is 5-methyl-1,3,4-thiadiazole-2-thiomethylthiocyanate.

4. The method as claimed in claim 1 wherein the active compound is 5-η-propyl-1,3,4-oxadiazole-2-thiomethylthiocyanate.

5. The method as claimed in claim 1 wherein the active compound is 5-η-pentyl-1,3,4-oxadiazole-2-thiomethylthiocyanate.

6. The method as claimed in claim 1 wherein the active compound is 5-η-nonanoyl-1,3,4-oxadiazole-2-thiomethylthiocyanate.

7. The method of claim 1 wherein the active compound is present in the composition in an amount from about 1 weight percent to about 30 weight percent.

* * * * *